United States Patent [19]

Higashii et al.

[11] Patent Number: 5,326,871

[45] Date of Patent: Jul. 5, 1994

[54] OPTICALLY ACTIVE PYRIMIDINE COMPOUND, PROCESS FOR PRODUCING THE SAME AND LIQUID CRYSTAL COMPOSITION CONTAINING THE SAME

[75] Inventors: Takayuki Higashii, Takatsuki; Shoji Toda, Ibaraki; Masayoshi Minai, Moriyama; Chizu Sekine, Tsukuba; Takeshi Tani, Tsukuba; Koichi Fujisawa, Tsukuba, all of Japan

[73] Assignee: Sumitomo Chemical Company, Limited, Osaka, Japan

[21] Appl. No.: 992,027

[22] Filed: Dec. 17, 1992

[30] Foreign Application Priority Data

Dec. 26, 1991 [JP] Japan .................................. 3-344604

[51] Int. Cl.⁵ ...................... C07D 239/02; C09K 19/34
[52] U.S. Cl. .................... 544/298; 544/315; 252/299.61
[58] Field of Search .................... 544/298, 315; 252/299.61

[56] References Cited

U.S. PATENT DOCUMENTS 4,943,385 7/1990 Inoue et al. .......................... 544/335
5,100,578 3/1992 Saito et al. .......................... 544/298
5,110,496 5/1992 Mogamiya et al. .................. 544/298

FOREIGN PATENT DOCUMENTS 0434297 6/1991 European Pat. Off. .
0435632 7/1991 European Pat. Off. .
3-31243 2/1991 Japan .

OTHER PUBLICATIONS

*Chemical Abstracts*, vol. 115, No. 22, Dec. 2, 1991, Columbus, Ohio, U.S.; Abstract No. 244215, p. 837.

*Primary Examiner*—Mukund J. Shah
*Assistant Examiner*—P. K. Sripada
*Attorney, Agent, or Firm*—Stevens, Davis, Miller & Mosher

[57] ABSTRACT

An optically active pyrimidine compound represented by general formula (I):

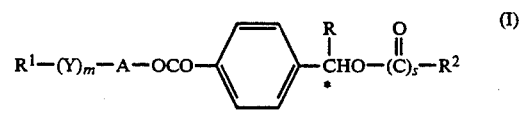

wherein R represents a fluoroalkyl group having 1 or 2 carbon atom(s), $R^1$ represents an alkyl group having 1-15 carbon atoms or an alkoxyalkyl group having 2-15 carbon atoms, both the alkyl and alkoxyalkyl groups being optionally substituted by halogen atom, Y represents —O—, —COO— or —OCO—, A represents:

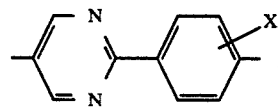

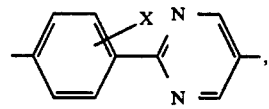

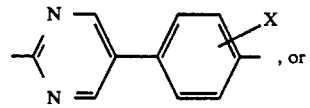

, or

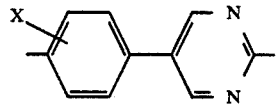

wherein X represents a hydrogen atom or a halogen atom, m and s each represent 0 or 1, and the C* means an asymmetric carbon atom; a process for producing said pyrimidine compound; and a liquid crystal composition containing said pyrimidine compound.

10 Claims, No Drawings

OPTICALLY ACTIVE PYRIMIDINE COMPOUND, PROCESS FOR PRODUCING THE SAME AND LIQUID CRYSTAL COMPOSITION CONTAINING THE SAME

This invention relates to optically active pyrimidine compounds, a process for producing said pyrimidine compounds and liquid crystal compositions containing and pyrimidine compounds. The pyrimidine compounds are useful as liquid crystal compounds.

Today, twisted nematic (hereinafter simply referred to as TN) type liquid crystal display element is most widely used as a liquid crystal display element. The TN type liquid crystal display element has many merits such as low driving voltage, small consumption of electric power, etc. However, the TN type liquid crystal display element is inferior to the light emission type display elements such as cathode-ray tube, electroluminescence, plasma displays and the like in the speed of response. Although a new TN type liquid crystal display element in which the twist angle of liquid crystal is altered to 180° to 270° has been developed, it is still insufficient in the response speed. In spite of various endeavors to make improvement, no TN type liquid crystal display element high in response speed has yet been obtained.

A new liquid crystal display element using a ferroelectric liquid crystal is actively studied currently, and it has a possibility of great improvement in the response speed (Clark et al.; Applied Phys. Lett., 36, 899 (1980)). This liquid crystal display element utilizes a chiral smectic phase such as chiral smectic C (hereinafter simply referred to as Sc*) phase exhibiting a ferroelectricity, or the like. As the phases exhibiting a ferroelectricity, chiral smectic F, G, H and I phases are also known in addition to the Sc* phase. A ferroelectric liquid crystal material to be used in an actual ferroelectric liquid crystal display element is requested to have a number of special characteristic properties. At the present time, however, there is known no compound satisfying all these requirements, and therefore ferroelectric liquid crystal compositions prepared by mixing together a plurality of liquid crystal compounds or non-(liquid crystal) compounds are necessarily used.

Apart from the ferroelectric liquid crystal compositions consisting of ferroelectric liquid crystal compounds only, Japanese Patent Application KOKAI (Laid-Open) No. 61-195187 disclosed a ferroelectric liquid crystal composition obtained by mixing a compound or a composition assuming a non-chiral smectic C, F, G, H or I phase (hereinafter these phases are generically referred to as "Sc phase etc.") as a fundamental material with one or more compounds assuming a ferroelectric liquid crystal phase. Further, it is reported in Mol. Cryst. Liq. Cryst., 89, 327 (1982) that a liquid crystal composition exhibiting a ferroelectricity as a whole can be prepared by mixing a compound or a composition assuming Sc phase etc. as a fundamental material with one or more compounds which are optically active and assume no ferroelectricity.

Taking these facts into consideration collectively, it can be understood that a ferroelectric liquid crystal composition can be constructed by using one or more optically active compounds as a fundamental material, no matter whether or not the optically active compounds assume a ferroelectricity.

Preferably, the optically active substance assumes a liquid crystal phase. When the optically active substance does not assume a liquid crystal phase, it is desirable that the optically active substance resembles a liquid crystal compound in structure, or it is the so-called pseudo liquid crystal substance.

Recently, liquid crystal compounds containing fluorine atoms have been found (Japanese Patent Application KOKAI (Laid-Open) No. 3-31243).

However, there has yet been found no liquid crystal material showing a spontaneous polarization necessary for a high response speed, having a low viscosity and keeping a ferroelectric liquid crystal phase over a wide temperature range involving the ambient temperature region, at the present stage.

Due to the increasing uses of liquid crystals in the current time, development of a liquid crystal having a novel structure is waited for. Thus, an object of this invention is to provide an optically active compound having a novel liquid crystal property in which a highly polar fluoroalkyl group is linked to an asymmetric carbon atom adjacent to a phenyl group.

Another object of this invention is to provide a process for producing said compound and a liquid crystal composition containing said compound.

A yet another object of this invention is to provide a liquid crystal element using said liquid crystal composition.

Further objects and effects of this invention will become apparent from the detailed description presented below.

This invention consists in a ferroelectric liquid crystal composition having a sufficient spontaneous polarization, capable of making a high-speed response and assuming a ferroelectric liquid crystal phase in the temperature range near ambient temperature, as well as optically active pyrimidine compounds useful as an ingredient of said composition and a process for producing said pyrimidine compounds.

Thus, this invention consists in optically active pyrimidine compounds represented by the following general formula (I):

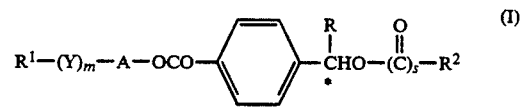

wherein R represents a $C_1$-$C_2$ fluoroalkyl group, $R^1$ represents a $C_1$-$C_{15}$ alkyl group, $R_2$ represents a $C_1$-$C_{15}$ alkyl group optionally substituted by halogen atom or a $C_2$-$C_{15}$ alkoxyalkyl group optionally substituted by halogen atom, Y represents —O—, —COO— or —OCO—, A represents:

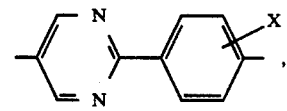

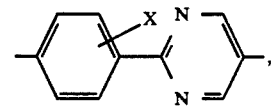

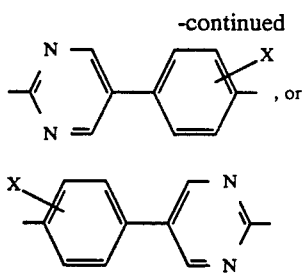

(X is hydrogen atom or halogen atom), m and s each represent 0 or 1, and C* represents an asymmetric carbon atom. Further, this invention consists in a process for producing said pyrimidine compounds, a liquid crystal composition containing at least one of the pyrimidine compounds and a liquid crystal element using said liquid crystal composition.

The optically active pyrimidine compound (I) of this invention can be produced by reacting a phenol derivative represented by the following general formula (II):

$R^1—(Y)_m—A—OH$ (II)

wherein $R^1$, A, Y and m are as defined above, with an optically active carboxylic acid represented by the following general formula (III):

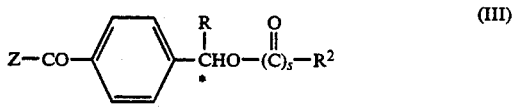

wherein Z represents a halogen atom or a hydroxyl group and R, $R^2$, s and C* are as defined above.

The substituent $R^1$ includes straight chain and branched chain forms of methyl, ethyl, propyl, butyl, pentyl, hexyl, heptyl, octyl, nonyl, decyl, undecyl, dodecyl, tridecyl, tetradecyl, pentadecyl and the like. Preferably, the substituent $R^1$ has 5 to 12 carbon atoms.

The substituent $R^2$ includes straight chain and branched chain forms of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, methoxymethyl, methoxyethyl, methoxypropyl, methoxybutyl, methoxypentyl, methoxyhexyl, methoxyheptyl, methoxyoctyl, methoxynonyl, methoxydecyl, ethoxymethyl, ethoxyethyl, ethoxypropyl, ethoxybutyl, ethoxypentyl, ethoxyhexyl, ethoxyheptyl, ethoxyoctyl, ethoxynonyl, ethoxydecyl, propoxymethyl, propoxyethyl, propoxypropyl, propoxybutyl, propoxypentyl, propoxyhexyl, propoxyheptyl, propoxyoctyl, propoxynonyl, propoxydecyl, butoxymethyl, butoxyethyl, butoxypropyl, butoxybutyl, butoxypentyl, butoxyhexyl, butoxyheptyl, butoxyoctyl, butoxynonyl, butoxydecyl, pentyloxymethyl, pentyloxyethyl, pentyloxypropyl, pentyloxybutyl, pentyloxypentyl, pentyloxyhexyl, pentyloxyheptyl, pentyloxyoctyl, pentyloxynonyl, pentyloxydecyl, hexyloxymethyl, hexyloxyethyl, hexyloxypropyl, hexyloxybutyl, hexyloxypentyl, hexyloxyhexyl, hexyloxyheptyl, hexyloxyoctyl, hexyloxynonyl, hexyloxydecyl, heptyloxymethyl, heptyloxyethyl, heptyloxypropyl, heptyloxybutyl, heptyloxypentyl, octyloxymethyl, octyloxyethyl, octyloxypropyl, octyloxybutyl, octyloxypentyl, nonyloxymethyl, nonyloxyethyl, nonyloxypropyl, nonyloxybutyl, nonyloxypentyl, decyloxymethyl, decyloxyethyl, decyloxypropyl, decyloxybutyl, decyloxypentyl, 1-methylethyl, 1-methylpropyl, 1-methylbutyl, 1-methylpentyl, 1-methylhexyl, 1-methylheptyl, 1-methyloctyl, 2-methylpropyl, 2-methylbutyl, 2,3-dimethylbutyl, 2,2,3-trimethylbutyl, 2-methylpentyl, 3-methylpentyl, 2,3-dimethylpentyl, 2,4-dimethylpentyl, 2,3,3,4-tetramethylpentyl, 2-methylhexyl, 3-methylhexyl, 4methylhexyl, 2,5-dimethylhexyl, 2-methylheptyl, 2-methyloctyl, 2-trihalomethylpentyl, 2-trihalomethylhexyl, 2-trihalomethylheptyl, 2-haloethyl, 2-halopropyl, 3-halopropyl, 3-halo-2-methylpropyl, 2,3-dihalopropyl, 2-halobutyl, 3-halobutyl, 4-halobutyl, 2,3-dihalobutyl, 2,4-dihalobutyl, 3,4-dihalobutyl, 2-halo-3-methylbutyl, 2-halo-3,3-dihalobutyl, 2-halopentyl, 3-halopentyl, 4-halopentyl, 5-halopentyl, 2,4-dihalopentyl, 2,5-dihalopentyl, 2-halo-3-methylpentyl, 2-halo-4-methylpentyl, 2-halo-3-monomethylpentyl-4-methylpentyl, 2-halohexyl, 3-halohexyl, 4-halohexyl, 5-halohexyl, 6-halohexyl, 2-haloheptyl, 2-halooctyl, 2-(2-haloethoxy)ethyl, 2-(3-halopropoxy)ethyl, 2-(4-halobutoxy)ethyl, 2-(5-halopentyloxy)ethyl, 2-(5-halohexyloxy)ethyl, 3-(2haloethoxy)propyl, 3-(3-halopropoxy)propyl, 3-(4-halobutoxy)propyl, 3-(5-halopentyloxy)propyl, 4-(2-haloethoxy)butyl, 4-(3-halopropoxy)butyl, 4-(4-halobutoxy)butyl, 5-(2-haloethoxy)pentyl, 5-(3-halopropoxy)pentyl, 6-(2-haloethoxy)hexyl and the like, provided that the term "halo" in the alkyl groups means fluorine, chlorine, bromine or iodine.

When the pyrimidine compound is used as a constituent of a liquid crystal, $R^2$ is preferably an alkyl or alkoxyalkyl group containing no halogen atom.

Said alkyl group preferably has 1–8 carbon atoms.

The fluoroalkyl group having 1 or 2 carbon atoms represented by R includes fluoromethyl, difluoromethyl, trifluoromethyl, 2-fluoroethyl, 2,2-difluoroethyl, and 2,2,2-trifluoroethyl.

The starting material represented by the formula (II) is a known compound and the other starting material represented by the formula (III) can be obtained according to the following scheme.

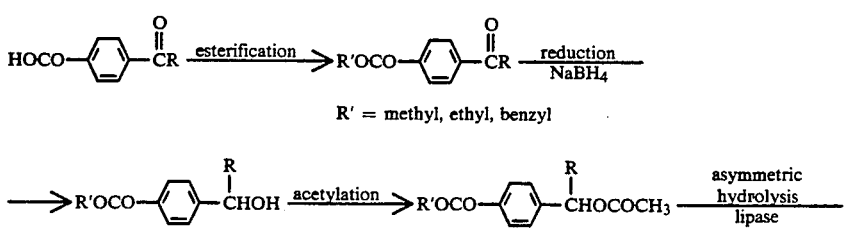

R' = methyl, ethyl, benzyl

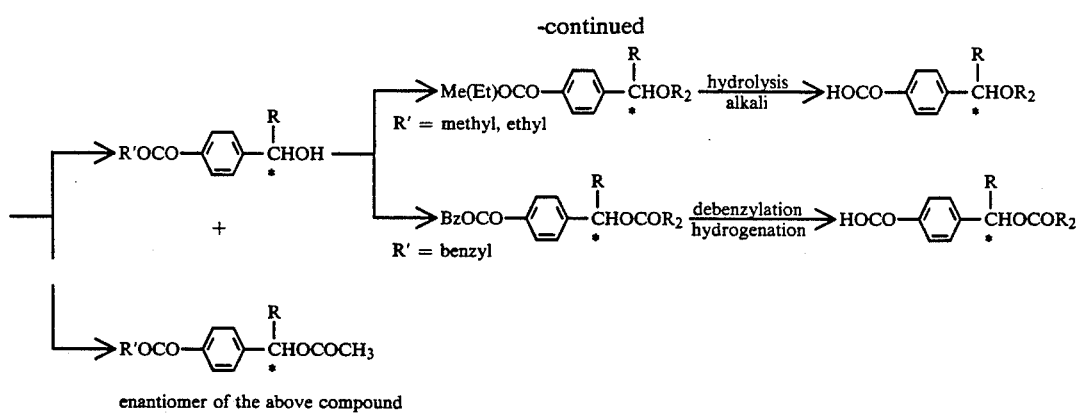

enantiomer of the above compound

The reaction between the optically active carboxylic acid (III) and phenol derivative (II) can be carried out according to the usual method of esterification. The reaction can be effected in the presence or absence of a solvent, using a catalyst or a condensing agent.

When a solvent is used in this reaction, the solvents which can be used include single members and mixtures of solvents inert to the reaction such as aliphatic and aromatic hydrocarbons, ethers, halogenated hydrocarbons, organic amines and the like, of which specific examples include tetrahydrofuran, ethyl ether, acetone, methyl ethyl ketone, toluene, benzene, chlorobenzene, dichloromethane, dichlorethane, chloroform, carbon tetrachloride, dimethylformamide, hexane, pyridine and the like. The quantity of the solvent used in this reaction is not critical.

In this reaction, it is preferable to use the phenol derivative (II) in an equal or an excessive amount to the optically active carboxylic acid (III), because thereby the relatively expensive optically active carboxylic acid (III) can be used effectively. Thus, the phenol derivative (II) is used usually in an amount of 1-4 equivalents and preferably in an amount of 1-2 equivalents, per equivalent of the optically active carboxylic acid (III). When a catalyst is used, the catalysts usable include organic and inorganic basic substances such as dimethylaminopyridine, tri-n-butylamine, pyridine, lysine, imidazole, sodium carbonate, sodium methylate, potassium hydrogen carbonate and the like. Organic and inorganic acids such as toluenesulfonic acid, methanesulfonic acid, sulfuric acid and the like are also usable as a catalyst.

The quantity of the catalyst cannot be specified, because it varies depending on the kinds of starting materials used, the combination of catalysts, etc. When an acid halide is used as the starting compound, for example, a basic substance as a catalyst can be used in a quantity of one equivalent or above based on the acid halide.

When the optically active carboxylic acid (III) is a carboxylic acid, the condensing agents which can preferably be used include carbodiimides such as N,N'-dicyclohexylcarbodiimide, N-cyclohexyl-N'-(4-diethylamino)cyclohexylcarbodiimide and the like. If desired, an organic base such as 4-pyrrolidinopyridine, pyridine, triethylamine and the like can also be used in combination therewith. In this case, the condensing agent is used usually in a quantity of 1-1.2 equivalents per equivalent of the optically active carboxylic acid (III). When an organic base is used in combination, the organic base is used in a quantity of 0.01-0.2 equivalent per equivalent of the condensing agent.

In the reaction between the optically active carboxylic acid (III) and phenol derivative (II), the reaction temperature is usually −30° C. to 100° C., and preferably −25° C. to 80° C. The reaction time is not critical, and the disappearance of starting optically active carboxylic acid (III) can be taken as the end of reaction.

After the reaction, the objective optically active pyrimidine compound (I) can be isolated from the reaction mixture by usual separating means, such as extraction, liquid phase separation, concentration, etc. If desired, the product can be purified by column chromatography, recrystallization, etc.

According to the process described above, an optically active pyrimidine compound (I) can be obtained.

The liquid crystal composition of this invention contains at least one optically active pyrimidine compound represented general formula (I) as its ingredient. The liquid crystal composition contains the optically active pyrimidine compound (I) in a quantity of 0.1–99.9% by weight, and particularly preferably 1–99% by weight. As the remainder, ingredients which are well known to those who are skilled in the art are used. The liquid crystal composition is effectively utilizable as an liquid crystal element, such as light switching element according to the well known methods. The method for its use is not critical.

The optically active pyrimidine compound represented by general formula (I) has quite excellent characteristic properties as a liquid crystal compound. Particularly those having an Sc* phase are effective for broadening the temperature range of Sc* phase when used as one ingredient of liquid crystal composition. Further, even if a compound cannot assume Sc* phase in itself alone, it can effectively be used as an ingredient for inducing a spontaneous polarization of liquid crystal composition. Accordingly, the optically active pyrimidine compound (I) of this invention is effectively applicable to a liquid crystal composition or a liquid crystal element using it. Further, according to the process of this invention, an optically active pyrimidine compound (I) can be obtained easily in a high yield, and the process is advantageously applicable industrially.

Next, this invention is explained below more concretely by way of the following examples. This invention is by no means limited by these examples.

EXAMPLE 1

In 20 ml of dry dichloromethane were dissolved 3.04 g (10 millimoles) of (+)-4-(1-hexyloxy-2,2,2-trifluoroethyl)benzoic acid, 3.28 g (10 millimoles) of 5-decyloxy-1-(p-hydroxyphenyl)pyrimidine and 0.2 g of 4-pyrrolidinopyridine. Then, 2.5 g (12 millimoles) of dicyclohexylcarbodiimide was added, and the resulting mixture was stirred at room temperature for 6 hours. After the reaction, 5% aqueous solution of acetic acid was added, and the whole was extracted with dichloromethane. The organic layer was washed successively with water and 7% aqueous solution of sodium hydrogen carbonate and dried on anhydrous magnesium sulfate, and then the solvent was distilled off, and the residue was purified by silica gel column chromatography. Thus, 5.0 g (yield 82%) of optically active 5-decyloxy-2-(p-hydroxyphenyl)pyrimidine (+)-4-(1-hexyloxy-2,2,2-trifluoroethyl)benzoate was obtained.

Phase series

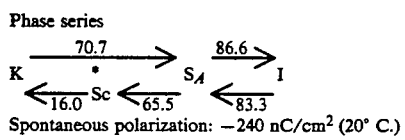

Spontaneous polarization: $-240$ nC/cm$^2$ (20° C.)

EXAMPLE 2

In 20 ml of dry dichloromethane were dissolved 3.04 g (10 millimoles) of optically active (+)-4-(1-hexyloxy-2,2,2-trifluoroethyl)benzoic acid, 3.00 g (10 millimoles) of 5-octyloxy-2-(p-hydroxyphenyl)pyrimidine and 0.2 g of 4-pyrrolidinopyridine. Then, 2.5 g (12 millimoles) of dicyclohexylcarbodiimide was added and the resulting mixture was stirred at room temperature for 6 hours. After the reaction, 5% aqueous solution of acetic acid was added and the whole was extracted with dichloromethane. The organic layer was washed successively with water and 7% aqueous solution of sodium hydrogen carbonate and dried on anhydrous magnesium sulfate, and then the solvent was distilled off and the residue was purified by silica gel column chromatography. Thus, 4.75 g (yield 81%) of optically active 5-octyloxy-2-(p-hydroxyphenyl)pyrimidine (+)-4-(1-hexyloxy-2,2,2-trifluoroethyl)benzoate was obtained.

Phase series

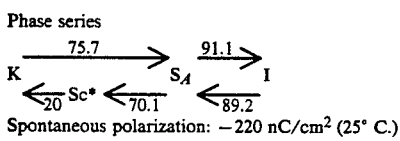

Spontaneous polarization: $-220$ nC/cm$^2$ (25° C.)

EXAMPLE 3

In 20 ml of dry dichloromethane were dissolved 3.04 g (10 millimoles) of optically active (+)-4-(1-hexyloxy-2,2,2-trifluoroethyl)benzoic acid, 3.12 g (10 millimoles) of 5-decyl-2-(p-hydroxyphenyl)pyrimidine and 0.2 g of 4-pyrrolidinopyridine. Then, 2.5 g (12 millimoles) of dicyclohexylcarbodiimide was added and the resulting mixture was stirred at room temperature for 6 hours. After the reaction, 5% aqueous solution of acetic acid was added and the whole was extracted with dichloromethane. The organic layer was washed successively with water and 7% aqueous solution of sodium hydrogen carbonate and dried on anhydrous magnesium sulfate, and then the solvent was distilled off and the residue was purified by silica gel column chromatography. Thus, 4.97 g (yield 83%) of optically active 5-decyl-2-(p-hydroxyphenyl)pyrimidine (+)-4-(1-hexyloxy-2,2,2-trifluoroethyl)benzoate was obtained.

$[\alpha]_D^{25} = -25.0$ (CHCl$_3$, C=1.5)

EXAMPLE 4

In 20 ml of dry dichloromethane were dissolved 3.04 g of (10 millimoles) of optically active (+)-4-(1-hexyloxy-2,2,2-trifluoroethyl)benzoic acid, 3.28 g (10 millimoles) of 2-decyloxy-5-(p-hydroxyphenyl)pyrimidine and 0.2 g of 4-pyrrolidinopyridine. Then, 2.5 g (12 millimoles) of dicyclohexylcarbodiimide was added and the resulting mixture was stirred at room temperature for 6 hours. After the reaction, 5% aqueous solution of acetic acid was added and the whole was extracted with dichloromethane. The organic layer was washed successively with water and 7% aqueous solution of sodium hydrogen carbonate and dried on anhydrous magnesium sulfate, and then the solvent was distilled off and the residue was purified by silica gel column chromatography. Thus, 5.05 g (yield 82%) of optically active 2-decyloxy-5-(p-hydroxyphenyl)pyrimidine (+)-4-(1-hexyloxy-2,2,2-trifluoroethyl)benzoate was obtained.

EXAMPLE 5

The compounds shown in Table 1 can be synthesized by procedures similar to those in the examples presented above.

TABLE 1

| No. | R$^1$ | Y | m | A | R | S | R$^2$ |
|-----|-------|---|---|---|---|---|-------|
| 1 | C$_8$H$_{17}$ | 0 | 1 | (pyrimidine-phenyl) | CF$_3$ | 0 | C$_6$H$_{13}$ |
| 2 | C$_{10}$H$_{21}$ | " | " | " | " | " | " |
| 3 | " | " | " | " | " | " | C$_3$H$_7$ |
| 4 | C$_5$H$_{11}$ | — | 0 | " | " | " | C$_6$H$_{13}$ |
| 5 | C$_{10}$H$_{21}$ | " | " | " | " | " | " |
| 6 | " | " | " | " | " | 1 | CH$_3$ |
| 7 | " | " | " | " | " | " | C$_5$H$_{11}$ |
| 8 | C$_5$H$_{11}$ | " | " | (phenyl-pyrimidine) | " | 0 | C$_3$H$_7$ |
| 9 | " | " | " | " | " | " | C$_6$H$_{13}$ |
| 10 | " | " | " | " | " | " | C$_8$H$_{17}$ |
| 11 | C$_7$H$_{15}$ | " | " | " | " | " | C$_6$H$_{13}$ |

TABLE 1-continued

| No. | R¹ | Y | m | A | R | S | R² |
|---|---|---|---|---|---|---|---|
| 12 | $C_{10}H_{21}$ | " | " | " | " | " | " |
| 13 | $C_{12}H_{25}$ | 0 | 1 | (pyrimidine-phenyl) | $CF_3$ | 0 | $C_3H_7$ |
| 14 | " | " | " | " | " | " | $C_5H_{11}$ |
| 15 | " | " | " | " | " | 1 | $C_3H_7$ |
| 16 | " | " | " | " | " | " | $C_5H_{11}$ |
| 17 | $C_{10}H_{21}$ | — | 0 | " | " | 0 | $-(CH_2)_3OE_t$ |
| 18 | " | " | " | " | " | 1 | $-(CH_2)_3CH(CH_3)_2$ |
| 19 | $C_{10}H_{21}$ | — | 0 | (pyrimidine-phenyl) | $CF_3$ | 1 | $-(CH_2)_2-F$ |
| 20 | " | " | " | (phenyl-pyrimidine) | " | 0 | $-(CH_2)_4OE_t$ |
| 21 | $C_8H_{21}$ | 0 | 1 | (pyrimidine-phenyl with F) | " | " | $C_3H_7$ |
| 22 | $C_{10}H_{21}$ | " | " | " | " | " | $C_6H_{13}$ |

Using the liquid crystal compounds of this invention, a liquid crystal composition shown in Table 2 was prepared. It was prepared by weighing out desired quantities of the compounds and mixing them together while heating and melting them in a sample bottle.

having a diameter of 2 μm as a spacer. Then, the above-mentioned liquid crystal composition was sealed into the cell in vacuum to obtain a liquid crystal element. The liquid crystal element was combined with a polarizer, an electric field of 20 V was applied thereto, and

TABLE 2

| Liquid crystal composition (ingredients) | Property |
|---|---|
| $C_{10}H_{21}O$—(pyrimidine)—(phenyl)—OCO—(phenyl)—$CHOC_6H_{13}$ with $CF_3$ <br> (10% by wt.) | Spontaneous polarization 14 nC/cm² |
| $C_{10}H_{21}O$—(phenyl)—COO—(phenyl)—$O(CH_2)_3CHC_2H_5$ with $CH_3$ <br> (90% BY WT.) | |
| Known compound <br> Spontaneous polarization: 0.2 nC/cm² | |

Method for Preparation of Liquid Crystal Element

A polyimide type polymer film was provided on a glass substrate equipped with an indium oxide transparent electrode. After rubbing the film in one direction, a liquid crystal cell was constructed from two glass substrates so that the directions of rubbing of the two sheets became parallel to each other, by using a glass fiber the change in the intensity of transmitting light was observed. As a result, it was found that this liquid crystal element can be used as a switching element.

COMPARATIVE EXAMPLE

Spontaneous polarizations of a compound of this invention and a few known compounds are as follows.

TABLE 3

| Compound | Formula | Phase series | Spontaneous polarization |
|---|---|---|---|
| The compound of Example 1 | C₁₀H₂₁O—[pyrimidine]—[phenyl]—OCO—[phenyl]—CHOC₆H₁₃ with CF₃ | K ⇌(70.7/16.0) S_A ⇌(86.6/83.3) I; Sc* ⇌63.5 | 240 nC/cm² (20° C.) |
| Comparative Compound 1 | C₁₀H₂₁O—[pyrimidine]—[phenyl]—COO—[phenyl]—CHOC₆H₁₃ with CF₃ | K ⇌(73.4/56.4) S_A ⇌(85.8/85.8) I; Sc* ⇌65 | 119 nC/cm² (57° C.) |
| Comparative Compound 2 | C₁₀H₂₁O—[phenyl]—[phenyl]—COO—[phenyl]—CHOC₆H₁₃ with CF₃ | Sc* ⇌(57.9/15.8) S_A ⇌(86.9/83.2) ⇌(92.9/91.6) I | 105 nC/cm² (40° C.) |

Although the compound of Example 1 is monotropic, its spontaneous polarization is more than twice as great as those of Comparative Compounds 1 and 2.

What is claimed is:

1. An optically active pyrimidine compound represented by the following general formula (I):

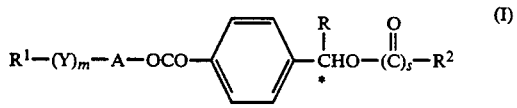

wherein R represents a fluoroalkyl group having 1 or 2 carbon atom(s); $R^1$ represents an alkyl group having 1–15 carbon atoms; $R^2$ represents an alkyl group having 1–15 carbon atoms or an alkoxyalkyl group having 2–15 carbon atoms, both the alkyl and alkoxyalkyl groups being optionally substituted by halogen atom; Y represents, —O—, —COO— or —OCO—; A is selected from the group consisting of:

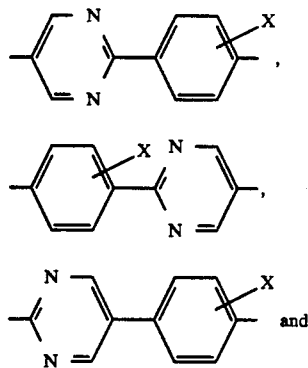

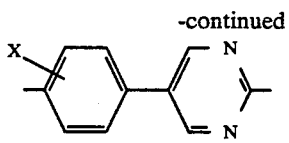

wherein X represents a hydrogen atom or a halogen atom; m and s each represent 0 or 1; and C* represents an asymmetric carbon atom.

2. A pyrimidine compound according to claim 1, wherein $R^2$ is an alkyl group having 1–15 carbon atoms or an alkoxyalkyl group having 2–15 carbon atoms.

3. A pyrimidine compound according to claim 1, wherein $R^1$ is an alkyl group having 5–12 carbon atoms and $R^2$ is an alkyl group having 1–8 carbon atoms.

4. A pyrimidine compound according to claim 3, wherein A is

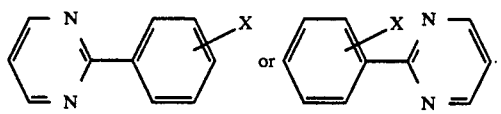

5. 5-Decyloxy-2-(p-hydroxyphenyl)pyrimidine (+)-4-(1-hexyloxy-2,2,2-trifluoroethyl)benzoate.

6. 5-Octyloxy-2-(p-hydroxyphenyl)pyrimidine (+)-4-(1-hexyloxy-2,2,2-trifluoroethyl)benzoate.

7. 5-Decyl-2-(p-hydroxyphenyl)pyrimidine (+)-4-(1-hexyloxy-2,2,2-trifluoroethyl)benzoate.

8. 2-Decyloxy-5-(p-hydroxyphenyl)pyrimidine (+)-4-(1-hexyloxy-2,2,2-trifluoroethyl)benzoate.

9. A liquid crystal composition comprising at least two components at least one of which is an optically active pyrimidine compound according to claim 1.

10. A liquid crystal display element using a liquid crystal composition containing at least one optically active pyrimidine compound according to claim 1.

* * * * *